United States Patent [19]

Fries

[11] Patent Number: 5,118,698
[45] Date of Patent: Jun. 2, 1992

[54] PHARMACEUTICAL PREPARATIONS

[75] Inventor: Walter Fries, Illertissen, Fed. Rep. of Germany

[73] Assignee: Heinrich Mack Nachf, Illertissen, Fed. Rep. of Germany

[21] Appl. No.: 618,438

[22] Filed: Nov. 27, 1990

[30] Foreign Application Priority Data

Nov. 29, 1989 [DE] Fed. Rep. of Germany ....... 3939492

[51] Int. Cl.⁵ .............................................. A61K 31/41
[52] U.S. Cl. ................................................... 514/359
[58] Field of Search ......................................... 514/359

[56] References Cited

FOREIGN PATENT DOCUMENTS 0095897 5/1983 European Pat. Off.
0096569 6/1983 European Pat. Off.

OTHER PUBLICATIONS

Hagers Handbuch der Pharmazentischen Proxis 4th edition, vol. 7, 1971.
Procardia Xl, Renese, Renese R, Robaxin, Depo-Medrol, Aristocort, Depo-Provera and Ativan excerpts from Physician's Desk Reference.
Journal of Pharmaceutical Sciences, 56 (3), 351 (1967).
Handbook of Pharmaceutical Excipients American Pharmaceutical Ass'n, 1986, pp. 209-213.
Journal of Pharmaceutical Sciences, 52, 917ff (1963).
Tieraerztlich Rundschau, 42, 912ff (1987) Catalogue of Pharmaceutical Adjuvents (entitled Polyaethylenglkole (flüssig)).

Primary Examiner—S. J. Friedman
Attorney, Agent, or Firm—Peter C. Richardson; Paul H. Ginsburg; Grover F. Fuller, Jr.

[57] ABSTRACT

A pharmaceutical preparation for parenteral administration of a drug consisting of a solvent system containing:

(a) 0 to 65% by weight of α-tetrahydrofurfuryl-ω-hydroxy-polyoxyethylene;
(b) 10 to 100% by weight polyethylene glycol with a mean molecular weight of 200 to 600; and
(c) 0 to 35% by weight of water The sum of components (a) and (b) amounting to at least 65% by weight, and one or more therapeutically active compounds of the formula

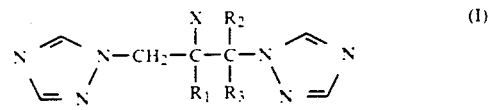

wherein $R_1$ denotes a phenyl radical optionally substituted with 1 to 3 substituents independently selected from the group consisting of F, Cl, Br, I, $CF_3$, $C_1$ to $C_4$ alkyl, and $C_1$ to $C_4$ alkoxy, or 5-chloro-pyrid-2-yl; X denotes OH, F, Cl or Br; $R_2$ is H, $CH_3$ or F; and $R_3$ is H or F.

15 Claims, No Drawings

PHARMACEUTICAL PREPARATIONS

FIELD OF THE INVENTION

The present invention relates to pharmaceutical preparations of certain therapeutically active triazole compounds.

BACKGROUND OF THE INVENTION

Various therapeutically active substances are not able to be administered in a pure form. It is frequently necessary to blend the active substances with other components so that a preparation is produced which is ready for use. Dependent on the chemical properties of the pharmacologically active substance it is necessary to take various considerations into account before a pharmaceutical preparation may be used for humans or animals.

When therapeutically active substances are to be administered parenterally it is usually necessary for the active substance in the form of a solid to be dissolved as a solution. Conventionally water is found to be a suitable solvent. If however the active substances are no more than sparingly soluble, it is not possible to produce any concentrated aqueous solutions for parenteral application, even though a comparatively high concentration of active substance would be desirable in order to avoid injection of an excessive volume which would not be well tolerated. In the art there has been a proposal to use cosolvents in order to bring sparingly soluble substances into solution. However, when more especially used in a highly concentrated form without or with only a small amount of added water, such cosolvents involve the disadvantage—more significantly in the case of intramuscular injections—of being poorly tolerated. There are then likely to be an induration (hardening of tissue), hemorrhage (bleeding) and/or necrosis (local death of tissue) at the injection site.

The use of tetrahydrofurfuryl alcohol polyethylene glycol as a solvent for parenteral preparations is mentioned in the Journal of Pharmaceutical Sciences, 52, page 917 ff (1963) where it is stated that undiluted application leads to irritation. This publication also describes the use of polyethylene glycols. It is stated here that the intramuscular injection of polyethylene glycol with a mean molecular weight of 300 may cause ischemic (bloodless) necroses in the muscular fascicle. These results were obtained from experiments on animals.

There is further literature confirming the view that polyethylene glycol should not be used in overly high concentrations. In a catalog of pharmaceutical adjuvants, which has been compiled by a working group organized by the companies Ciba-Geigy, Hoffmann-LaRoche and Sandoz, it is pointed out that the maximum concentration of polyethylene glycol with a mean molecular weight of 300 in solutions for parenteral administration amounts to about 30%. At a concentration in excess of 40% a hemolytic effect of polyethylene glycol with a mean molecular weight of 300 (PEG 300) was found to occur.

This finding has been also confirmed in Tieraerztliche Rundschau, 42, page 912 ff (1987) by O. Kern. It was found that the intramuscular injection of undiluted PEG 300 caused ischemic necrosis in rats. Furthermore it was found that an intramuscular injection of a 40% propylene glycol solution in water caused very pronounced tissue damage in various animals.

Thus it is to be seen from the prior art that different solvents may be utilized for parenteral preparations, if relatively low concentrations of these solvents are employed. The use of preparations which have a high percentage of such solvents may frequently lead to undesired side-effects.

The use of aqueous media for the pharmaceutical preparations is on the other hand not appropriate if the therapeutically active compound forms a sparingly soluble hydrate in the form of needles on contact with aqueous media. Thus in the case of therapeutically active compounds which are only sparingly soluble in water, more particularly triazole compounds, there is the danger of the hydrate crystallizing out in the form of needles. There is no need to explain that preparations intended for parenteral administration have to be in the form of a homogeneous solution without any possibility of crystallizing out from the solution.

Accordingly, one object of the present invention is to provide solvent mixtures which in the case of parenteral and more especially intramuscular administration are free of undesired side-effects while at the same time being capable of dissolving those therapeutically active substances, in a sufficient concentration and in stable manner, which are at the most only sparingly soluble in water.

SUMMARY OF THE INVENTION

The present invention relates to a pharmaceutical preparation consisting of a solvent system containing:

(a) 0 to 65% by weight of α-tetrahydrofurfuryl-ω-hydroxypoly(oxyethylene), (b) 10 to 100% by weight of polyethylene glycol with a mean molecular weight of 200 to 600, and (c) 0 to 35% by weight of water, the sum of the two components (a) and (b) amounting to at least 65% by weight, and one or more therapeutically active compounds which have a pronounced antimycotic activity. The compounds have the following formula (I):

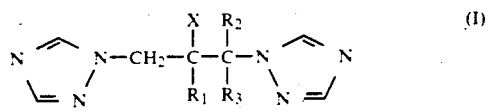

wherein $R_1$ denotes a phenyl radical optionally substituted with 1 to 3 substituents independently selected from the group consisting of F, Cl, Br, I, $CF_3$, $C_1$ to $C_4$ alkyl, and $C_1$ to $C_4$ alkoxy, or 5-chloro-pyrid-2-yl; X denotes OH, F, Cl or Br; $R_2$ is H, $CH_3$ or F; and $R_3$ is H or F.

Such solvent systems containing 10–45% by weight of α-tetrahydrofurfuryl-ω-hydroxypoly(oxyethylene), 10 to 90% by weight of polyethylene glycol and 0 to 35% by weight of water are preferably used. A more specific and more especially preferred composition is in the form of preparations which contain 30 to 55% by weight of polyethylene glycol, 35 to 45% by weight of α-tetrahydrofurfuryl-ω-hydroxypoly(oxyethylene) and 10 to 35% by weight of water. The sum of the two components α-tetrahydrofurfuryl-ω-hydroxypoly(oxyethylene) and polyethylene glycol amounts in every case to at least 65% by weight.

A group of compounds which may be used according to the invention are those with the formula

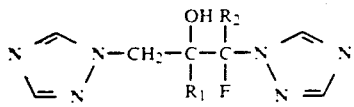

wherein $R_1$ is phenyl, optionally substituted with 1 to 3 substituents, each of them selected independently selected from the group consisting of F, Cl, Br, I, $CF_3$, $C_1$ to $C_4$ alkyl and $C_1$ to $C_4$ alkoxy, or 5-chloro-pyrid-2-yl, and $R_2$ is H, $CF_3$ or F. Such compounds are described in European Patent Application with the publication number 118245, the disclosure of which is hereby incorporated herein by reference. Preferably triazole derivatives are used as therapeutically active substances which have a pronounced antimycotic activity. The compounds have the following formula III

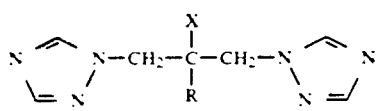

wherein R denotes a phenyl radical optionally substituted with 1 to 3 substituents selected from the group consisting essentially of F, Cl, Br, I and $CF_3$, and X denotes OH, F, Cl or Br. These compounds are described in more detail in the European patent application with the publication number 96,569.

Compounds which are particularly preferably used in the present invention include:
1,3-bis(1H-,2,4-triazol-1-yl) -2-bromo-2-(2,4-dichlorophenyl)-propane,
1,3-bis(1H-1,2,4-triazol-1-yl)-2-chloro-2-(2,4-dichlorophenyl)-propane,
1,3-bis(1H-1,2,4-triazol-1-yl)-2-(4-iodophenyl)propane-2-ol and
2,4-difluoro-α,α-bis(1H-1,2,4-triazol-1-ylmethyl)benzyl alcohol

DETAILED DESCRIPTION OF THE INVENTION

It has been found that the triazole compounds of formula I have a good solubility in a solvent system containing about O to about 65% by weight of α-tetrahydrofurfuryl-ω-hydroxypoly(oxyethylene), about 10 to about 100% by weight of polyethylene glycol and about O to about 35% by weight of water, the sum of the components α-tetrahydrofurfuryl-ω-hydroxypoly(oxyethylene) and polyethylene glycol being equal to at least about 65% by weight of the solvent system.

It was found, surprisingly, that despite the addition of up to 35% by weight of water to a solvent system containing α-tetrahydrofurfuryl-ω-hydroxypoly(oxyethylene) and polyethylene glycol, solvents with a content of up to 150 mg/ml of the bis-triazole derivative could be prepared. These solutions remained stable for a period of seven weeks at 4° C. without the hydrate crystallizing out.

Parenteral administration involves a daily dose of about 0.1 to about 5 mg of the bis-triazole derivative per kg body weight of the patient to comply with individual requirements of the person to be treated.

Furthermore contrary to the views so far expressed in the literature such solutions are very well tolerated when injected intramuscularly. This was proved with the aid of tests on rabbits and dogs. The cosolvents used are thus also well tolerated physiologically, especially when used with the bis-triazole derivative.

The polyethylene glycol used was one having a mean molecular weight between 200 and 600 and preferably between 300 and 400 or, more preferably, 300.

It was further found that solutions of bis-triazole compounds in polyethylene glycol were well tolerated. Even solutions with polyethylene glycol as the sole component, were well tolerated in the case of intramuscular administration. Hemorrhage was not found to occur in the tests on animals performed and it was only in isolated instances that there was temporary induration. Owing to the risk of hemolysis solutions of bis-triazole derivatives in pure polyethylene glycol could only be administered intramuscularly and could not be used intravenously.

The use of the solvent system in accordance with the invention led to injections with a viscosity of under 1000 mPas, this ensuring good injectability.

EXAMPLES OF PRODUCTION

EXAMPLE 1

5 g of 2,4-difluoro-α,α-bis(1H-1,2,4-triazol-1-ylmethyl)benzyl alcohol were dissolved while stirring in a mixture of 41 g of α-tetrahydrofurfuryl-ω-hydroxypoly(oxyethylene) and 30.8 g of polyethylene glycol 300. 30.8 g of distilled water were added to this solution. The solution was aerated with nitrogen during production and after sterilization by filtration was placed in ampoules, injection vials or pre-filled syringes with preceding and subsequent aeration by nitrogen.

EXAMPLE 2

10 g of 2,4-difluoro-α,α-bis(1H-1,2,4-triazol-1-ylmethyl)benzyl alcohol were dissolved while stirring in 102 g of polyethylene glycol with a mean molecular weight of 300. During production the solution was aerated with nitrogen and after sterilization by filtration was placed in ampoules, injection vials or pre-filled syringes with aeration by nitrogen before and afterwards.

EXAMPLE 3

10 g of 2,4-difluoro-α,α-bis(1H-1,2,4-triazol-1-ylmethyl)benzyl alcohol were dissolved while stirring in a mixture of 40.4 g of α-tetrahydrofurfuryl-ω-hydroxypoly(oxyethylene) and 60.6 g of polyethylene glycol 300. The solution was aerated with nitrogen during production and after sterilization by filtration was placed in ampoules, injection vials or pre-filled syringes with preceding and subsequent aeration by nitrogen.

I claim:
1. A pharmaceutical preparation consisting of a solvent system containing:
   (a) 0 to 65% by weight of α-tetrahydrofurfuryl-ω-hydroxypoly(oxyethylene),
   (b) 10 to 100% by weight of polyethylene glycol with a mean molecular weight of 200 to 600, and
   (c) 0 to 35% by weight of water, the sum of the two components (a) and (b) amounting to at least 65% by weight, and one or more therapeutically active compounds of the formula

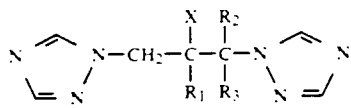

wherein $R_1$ denotes a phenyl radical optionally substituted with 1 to 3 substituents independently selected from the group consisting of F, Cl, Br, I, $CF_3$, $C_1$ to $C_4$ alkyl, and $C_1$ to $C_4$ alkoxy, or 5-chloro-pyrid-2-yl; X denotes OH, F, Cl or Br; $R_2$ is H, $CH_3$ or F; and $R_3$ is H or F.

2. The pharmaceutical preparation as claimed in claim 1, characterized in that it contains 10 to 45% by weight of α-tetrahydrofurfuryl-ω-hydroxypoly(oxyethylene).

3. The pharmaceutical preparation as claimed in claim 2, characterized in that it contains 35 to 45% by weight of α-tetrahydrofurfuryl-ω-hydroxypoly(oxyethylene).

4. The pharmaceutical preparation as claimed in claim 1, characterized in that it contains 10 to 90% by weight of polyethylene glycol.

5. The pharmaceutical preparation as claimed in claim 4, characterized in that it contains 30 to 55% by weight of polyethylene glycol.

6. The pharmaceutical preparation as claimed in claim 1, characterized in that the polyethylene glycol has a mean molecular weight of 300.

7. The pharmaceutical preparation as claimed in claim 1, characterized in that it is adapted to be parenterally administered.

8. The pharmaceutical preparation according to claim 1, characterized in that said pharmaceutically active component is a triazole derivative of the following formula III:

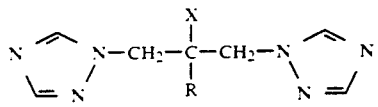

wherein R denotes a phenyl radical with, if desired, 1 to 3 substituents selected from the group consisting essentially of F, Cl, Br, I and $CF_3$, and X denotes OH, F, Cl or Br.

9. The pharmaceutical preparation as claimed in claim 8, characterized in that the said triazole derivative is 1,3,-bis(1H-1,2,4-triazol-1-yl)-2-bromo-2-(2,4-dichlorophenyl)-propane.

10. The pharmaceutical preparation as claimed in claim 8 characterized in that the triazole derivative is 1,3-bis(1H-1,2,4-triazol-1-yl)-2-chloro-2-(2,4-dichlorophenyl 11. The pharmaceutical preparation as claimed in claim 8, characterized in that the triazole derivative is 1,3-bis(1H-1,2,4-triazol-1-yl)-2-(4-iodophenyl) propane-2-ol.

12. The pharmaceutical preparation as claimed in claim 8, characterized in that the said triazole derivative is 2,4-difluoro-α,α-bis(1H-1,2,4-triazol-1-ylmethyl)benzyl alcohol.

13. The pharmaceutical preparation as claimed in claim 8, characterized in that it contains 30 to 100 mg/ml of the triazole derivative.

14. The pharmaceutical preparation as claimed in claim 8, characterized in that it contains 50 to 100 mg/ml of the triazole derivative.

15. The pharmaceutical preparation as claimed in claim 1 characterized in that it is in the form of ampoules, injection vials or pre-filled syringes.

* * * * *